US00PP23293P2

(12) United States Plant Patent
Fisher et al.

(10) Patent No.: US PP23,293 P2
(45) Date of Patent: Jan. 1, 2013

(54) ***MANDEVILLA* PLANT NAMED 'FGDIP1RV'**

(50) Latin Name: *Mandevilla splendens*
Varietal Denomination: FGDIP1RV

(75) Inventors: Wes Fisher, Sebring, FL (US); James E. DuBose, Sebring, FL (US)

(73) Assignee: Fury Genetics LLC, Hawthorne, FL (US)

( * ) Notice: Subject to any disclaimer, the term of this patent is extended or adjusted under 35 U.S.C. 154(b) by 36 days.

(21) Appl. No.: 13/134,170

(22) Filed: May 31, 2011

(51) Int. Cl.
*A01H 5/00* (2006.01)

(52) U.S. Cl. ..... Plt./232

(58) Field of Classification Search ..... Plt./232
See application file for complete search history.

*Primary Examiner* — Susan McCormick Ewoldt
(74) *Attorney, Agent, or Firm* — C. A. Whealy

(57) ABSTRACT

A new and distinct cultivar of *Mandevilla* plant named 'FGDIP1RV', characterized by its upright, outwardly spreading, moderately vining and relatively compact plant habit; freely branching habit, dense and bushy appearance; green, yellow green and pale yellow variegated leaves; dark red-colored flowers; and year-round flowering habit.

2 Drawing Sheets

Botanical designation: *Mandevilla splendens.*
Cultivar denomination: 'FGDIP1RV'.

BACKGROUND OF THE INVENTION

The present invention relates to a new and distinct cultivar of *Mandevilla* plant, botanically known as *Mandevilla splendens* and hereinafter referred to by the name 'FGDIP1RV'.

The new *Mandevilla* plant is a naturally-occurring branch mutation of *Mandevilla splendens* 'DIP 79', disclosed in U.S. Plant Pat. No. 19,698. The new *Mandevilla* plant was discovered and selected by the Inventors on a single plant within a population of plants of 'DIP 79' grown in a controlled greenhouse environment in Sebring, Fla. on May 18, 2010. The new *Mandevilla* plant was selected on the basis of its unique leaf variegation.

Asexual reproduction of the new *Mandevilla* plant by tip cuttings in a controlled greenhouse in Sebring, Fla. since May 19, 2010, has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'FGDIP1RV'. These characteristics in combination distinguish 'FGDIP1RV' as a new and distinct *Mandevilla* plant:

1. Upright, outwardly spreading, moderately vining and relatively compact plant habit.
2. Freely branching habit, dense and bushy appearance.
3. Green, yellow green and pale yellow variegated leaves.
4. Dark red-colored flowers.
5. Year-round flowering habit.

Plants of the new *Mandevilla* differ primarily from plants of the parent, 'DIP 79', in leaf color as plants of 'DIP 79' have solid green-colored leaves.

Plants of the new *Mandevilla* can be compared to plants of the *Mandevilla sanderi* 'Monproud', disclosed in U.S. Plant Pat. No. 15,359. In side-by-side comparisons conducted in Sebring, Fla., plants of the new *Mandevilla* differed from plants of 'Monproud' in the following characteristics:

1. Plants of the new *Mandevilla* were less vining than plants of 'Monproud'.
2. Plants of the new *Mandevilla* were more outwardly spreading and broader than plants of 'Monproud'.
3. Plants of the new *Mandevilla* and 'Monproud' differed in leaf color as plants of 'Monproud' had pale yellow, green and greyed green-colored leaves.
4. Plants of the new *Mandevilla* were more freely flowering than plants of 'Monproud'.
5. Plants of the new had larger flowers than plants of 'Monproud'.
6. Plants of the new *Mandevilla* and 'Monproud' differed in flower color as plants of 'Monproud' had red purple-colored flowers.
7. Plants of the new *Mandevilla* had shorter sepals than plants of 'Monproud'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'FGDIP1RV' grown in a container.

The photograph on the second sheet is a close-up view of a typical flowering plant of 'FGDIP1RV'.

DETAILED BOTANICAL DESCRIPTION

Plants used for the aforementioned photographs and following description were grown during the winter and early spring in 1.5-gallon containers in a shaded polyethylenecovered greenhouse in Sebring, Fla. and under conditions which closely approximate commercial production conditions. During the production of the plants, day temperatures ranged from ranged from 24° C. to 38° C. and night temperatures ranged from 2° C. to 27° C. Plants were eight months old when the photographs and description were taken. Plants were pinched one time. In the following description, color references are made to The Royal Horticultural Society Colour Chart, 1966 Edition, except where general terms of ordinary dictionary significance are used.

Botanical classification: *Mandevilla splendens* 'FGDIP1RV'.

Parentage: Naturally-occurring branch mutation of *Mandevilla splendens* 'DIP 79', disclosed in U.S. Plant Pat. No. 19,698.

Propagation:

*Type*.—By tip cuttings.

*Time to initiate roots, summer*.—About three weeks at 29° C.

*Time to initiate roots, winter*.—About three weeks at 24° C.

*Time to produce a rooted young plant, summer*.—About 44 days at 29° C.

*Time to produce a rooted young plant, winter*.—About 50 days at 24° C.

*Root description*.—Fibrous, medium in thickness; white in color.

*Rooting habit*.—Freely branching; medium density.

Plant description:

*Plant and growth habit*.—Upright, outwardly spreading, moderately vining and relatively compact plant habit; moderately vigorous to vigorous growth habit; freely branching habit, primary lateral branches with secondary branches; dense and bushy appearance; pinching enhances lateral branch development.

*Plant height*.—About 96 cm; vines to 200 cm.

*Plant diameter* (*spread*).—About 96 cm.

*Lateral branch description*.—Length: About 30 cm. Diameter: About 3 mm. Internode length: About 7 mm to 4 cm. Strength: Flexible, strong. Texture, young stems: Smooth. Texture, developed stems: Woody. Color, young stems: Close to 183A to 183B; becoming closer to 145A with development. Color, woody stems: Close to 166A becoming closer to 197B to 197D with development.

Foliage description:

*Arrangement*.—Opposite, simple.

*Length*.—About 6.5 cm.

*Width*.—About 3.7 cm.

*Shape*.—Obovate.

*Apex*.—Cuspidate.

*Base*.—Obtuse.

*Margin*.—Entire.

*Texture, upper and lower surfaces*.—Smooth, glabrous.

*Venation pattern*.—Pinnate.

*Color*.—Developing leaves, upper surface: Random sectors of close to 39A, 39B, 37B and 177A; towards the apex, close to 150A. Developing leaves, lower surface: Close to 146A with random sectors of close to 148C, 148D, 147D, 10C and 10D. Fully expanded leaves, upper surface: Random sectors of close to 147A, 147C, 148D, 149B, 150D, 10C and 10D; venation, close to 145C. Fully expanded leaves, lower surface: Random sectors of close to 147A, 147C, 148D, 149B, 150D and 10D; venation, close to 149A to 149B.

*Petioles*.—Length: About 5 mm to 1.5 cm. Diameter: About 1.2 mm to 1.5 mm. Texture, upper and lower surfaces: Smooth, glabrous. Color, upper surface: Close to 149B; center, close to 39C. Color, lower surface: Close to 149B.

Flower description:

*Flower type and habit*.—Single salverform flowers; flowers arranged in loose terminal and axillary racemes; flowers face outwardly and upright; freely flowering habit with about 200 flowers developing per plant.

*Natural flowering season*.—Plants of the new *Mandevilla* flower continuously year-round in Florida.

*Flower longevity on the plant*.—Flowers last about seven to nine five days; flowers not persistent.

*Fragrance*.—Moderate, mint-like.

*Flowers*.—Appearance: Flared trumpet, corolla fused, five-parted; petals imbricate; flowers salverform and roughly star-shaped. Diameter: About 6 cm to 8 cm. Depth (length): About 5 cm to 6 cm. Throat diameter: About 1.5 cm. Tube length: About 4 cm to 5 cm. Tube diameter, base: About 1.7 mm to 2 mm.

*Flower buds*.—Length: About 4 cm. Diameter: About 1 cm. Shape: Cylindrical, pointed. Color: Distal half, close to 53B with longitudinal stripes, close to 155D; proximal half, close to 53A; central bands, 149B and 11D.

*Corolla*.—Arrangement: Single whorl of five petals, fused into flared trumpet; petals imbricate. Petal lobe length: About 2.5 cm to 3.5 cm. Petal lobe width: About 2 cm to 2.5 cm. Petal lobe shape: Roughly spatulate. Petal apex: Cuspidate. Petal margin: Entire. Petal texture, upper and lower surfaces: Smooth, glabrous; velvety. Throat and tube texture: Smooth, glabrous. Color: Petal, when opening, upper and lower surfaces: Close to varying shades of 53A, 53B, 46A and 46B. Petal, fully opened, upper surface: Close to varying shades of 53A, 53B, 46A and 46B; venation, close to 31A and 32A. Petal, fully opened, lower surface: Close to varying shades of 53A, 53B, 46A and 46B; venation, similar to surface color. Throat: Close to 21A to 21B; venation, close to 53B to 53C. Tube: Distal half, close to 53B with longitudinal stripes, close to 155D; proximal half, close to 53A; central bands, 149B and 11D; venation, close to 31A and 32A.

*Sepals*.—Arrangement and appearance: Five per flower in a single whorl; fused towards the base. Length: About 4.6 mm to 5 mm. Width: About 0.9 mm to 2.1 mm. Shape: Roughly deltoid. Apex: Acute. Margin: Entire. Texture, upper and lower surfaces: Smooth, glabrous. Color, upper surface: Close to 149B. Color, lower surface: Close to 149C.

*Peduncles*.—Length: About 3 cm. Diameter: About 2.5 mm. Texture: Smooth, glabrous. Strength: Flexible, but strong. Color: Close to 144D.

*Pedicels*.—Length: About 2 cm to 2.5 cm. Diameter: About 1.5 mm to 2 mm. Texture: Smooth, glabrous. Strength: Flexible, but strong. Color: Close to 145B.

*Reproductive organs*.—Stamens: Quantity and arrangement: Typically five; filaments fused to corolla; anthers, connivent. Filament length: About 2 cm. Filament color: Close to 155D. Anther shape: Elongated oblong. Anther length: About 3 mm. Anther color: Close to 11A. Pollen amount: Scarce. Pollen color: Close to 11A. Pistils: Quantity: Typically one. Pistil length: About 2.3 cm to 2.5 cm. Stigma shape: Oblong to rounded. Stigma color: Close to 11D. Style length: About 1.2 cm. Style color: Close to 155D. Ovary color: Close to 145A to 145B.

*Seeds and fruits*.—Seed and fruit production have not been observed on plants of the new *Mandevilla*.

Disease/pest resistance: Plants of the new *Mandevilla* have been noted to be somewhat resistant to Fusarium. Plants of the new *Mandevilla* have not been noted to resistant to pests and other pathogens common to *Mandevilla* plants.

Temperature tolerance: Plants of the new *Mandevilla* have been observed to tolerate temperatures from about 1° C. to about 43° C.

It is claimed:

1. A new and distinct *Mandevilla* plant named 'FGDIP1RV' as illustrated and described.

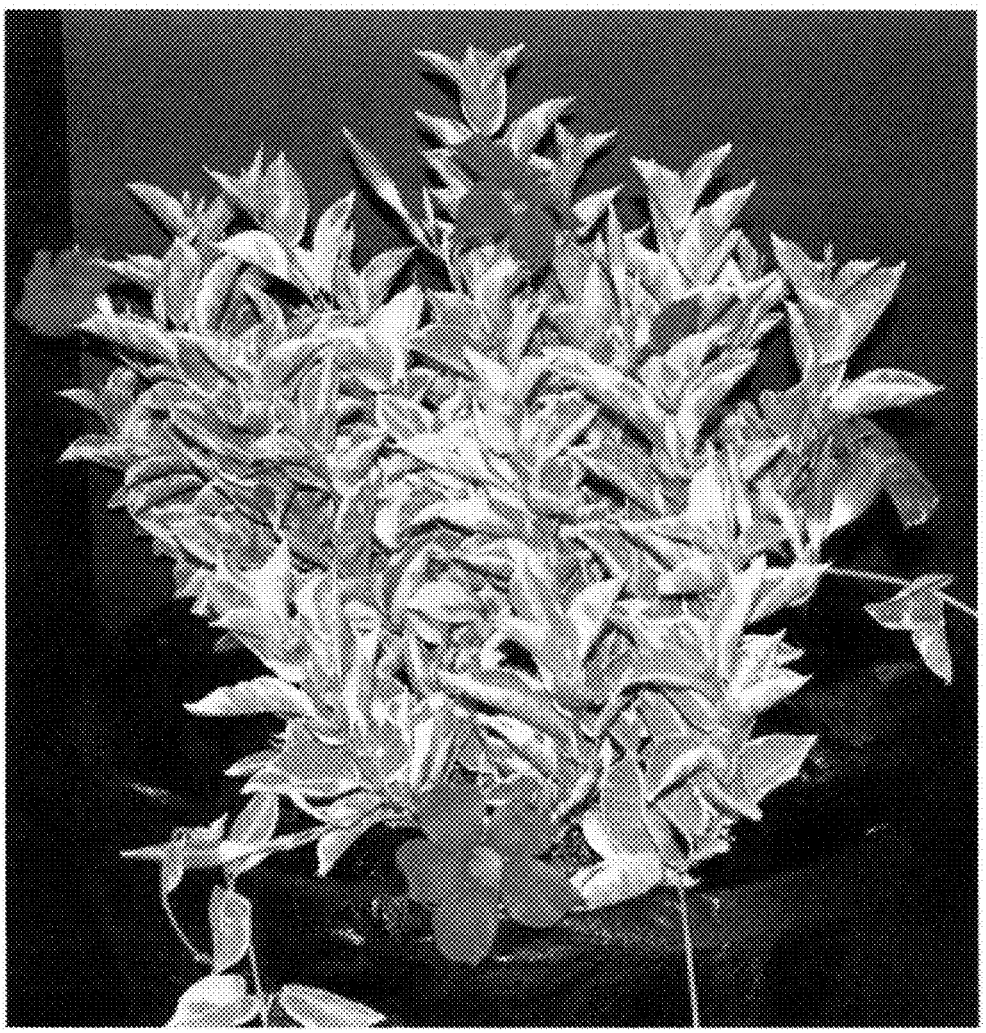

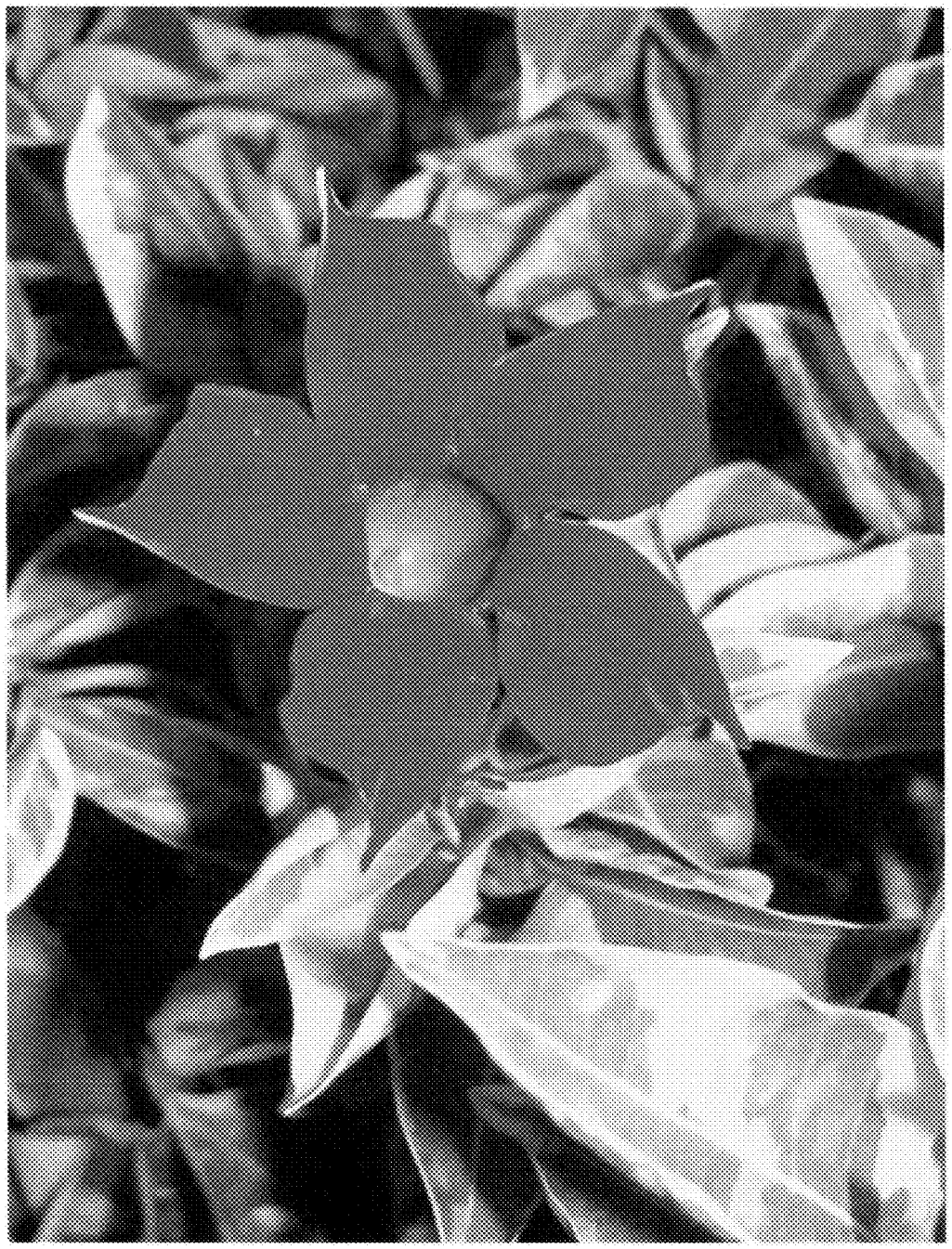

* * * * *